(12) United States Patent
Brojek et al.

(10) Patent No.: US 8,162,930 B2
(45) Date of Patent: Apr. 24, 2012

(54) METHOD AND THE DEVICE FOR CRYOGENIC THERAPY APPLIED ON THE WHOLE BODY OF A PATIENT

(75) Inventors: Wieslaw Brojek, Blalystok (PL); Wlodzimierz Szmurlo, Nieszawa (PL)

(73) Assignee: Metrum Cryoflex Spolka z organiczona odpowiedzialnoscia, Sp. k., Blizne Łaszczyńskiego (PL)

( * ) Notice: Subject to any disclaimer, the term of this patent is extended or adjusted under 35 U.S.C. 154(b) by 1355 days.

(21) Appl. No.: 11/808,379

(22) Filed: Jun. 8, 2007

(65) Prior Publication Data
US 2007/0293920 A1    Dec. 20, 2007

Related U.S. Application Data

(63) Continuation-in-part of application No. 10/494,619, filed as application No. PCT/PL01/00087 on Nov. 5, 2001, now Pat. No. 7,244,269.

(51) Int. Cl.
*A61B 18/02* (2006.01)
(52) U.S. Cl. .................................. 606/22; 606/20
(58) Field of Classification Search ............ 606/20, 606/21; 62/46.2, 50.2
See application file for complete search history.

(56) References Cited

U.S. PATENT DOCUMENTS

| 3,527,414 | A |   | 9/1970  | Schorsch |
|-----------|---|---|---------|----------|
| 3,648,474 | A | * | 3/1972  | Moline .............................. 62/64 |
| 4,838,270 | A |   | 6/1989  | Donnerhack et al. |
| 4,880,003 | A |   | 11/1989 | Donnerhack et al. |
| 5,729,983 | A | * | 3/1998  | Garrett et al. .................. 62/46.1 |
| 5,775,110 | A |   | 7/1998  | Waldron |

FOREIGN PATENT DOCUMENTS

| DE | 344 1 091 A1   | 5/1986  |
| DE | 195 15 287 A1  | 10/1996 |
| DE | 296 15 726 U1  | 11/1997 |
| DE | 3641293 A1     | 6/1998  |
| DE | 101 54 602 A1  | 5/2003  |
| EP | 0 226 107 A1   | 11/1986 |

* cited by examiner

*Primary Examiner* — Roy Gibson
(74) *Attorney, Agent, or Firm* — Blank Rome LLP

(57) ABSTRACT

The present invention relates to methods and devices for carrying out cryogenic therapy, particularly on the whole body of a patient, wherein the patient is exposed to gases cooled to cryogenic temperature. The process is performed by introducing the patient into the interior of a treatment cabin and exposing the body to cold air deposited into the cabin space.

12 Claims, 4 Drawing Sheets

US 8,162,930 B2

METHOD AND THE DEVICE FOR CRYOGENIC THERAPY APPLIED ON THE WHOLE BODY OF A PATIENT

This application is a continuation-in-part (CIP) of U.S. patent application Ser. No. 10/494,619, filed May 4, 2004, now U.S. Pat. No. 7,244,269 which is a U.S. National Phase of PCT/PL01/00087, filed Nov. 5, 2001.

FIELD OF THE INVENTION

The present invention relates to methods and the devices for carrying out the cryogenic therapy, particularly on the whole body of the patient, wherein the patient is exposed to the gases cooled to the cryogenic temperature. The process is performed by introducing the patient into the interior of the treatment cabin and exposing the body to the deposition of cold gases into the cabin space.

BACKGROUND OF THE INVENTION

There are known methods in medical technology for performing the cryogenic therapy by exposing certain parts of the human body or the whole body to the agents that reduces the temperature. These methods are generally carried out by using liquefied gases or compressed gases. Devices for carrying out the cryogenic treatment containing a therapeutic chamber are also known.

German Patent Specification No. 3213919 discloses a device for preparing cryogenic air which is provided to the medical cryogenic chamber. The device has an air compressor, a dryer for removing the steam from the compressed air, a heat exchanger and a liquefied gas container. The device is also provided with measuring elements, control elements and protective elements. The parts of the device which contain the cryogenic agents are provided within a thermal-insulated system. This device has several disadvantages, including long starting time and requiring a stand-by system.

Polish Patent Specification No. 157168 discloses a device for carrying out a cryogenic treatment which has a chamber for patients and a cryogenic air loading unit. The chamber has a loading air circulation system having an air compressor, a dryer and an air cooling circulation system. The cooling air circulation system has a liquefied gas vessel, and heat exchangers which include three gas heat exchangers, i.e., a preliminary heat exchanger, a main heat exchanger and a final heat exchanger; as well as the spraying element. The preliminary heat exchanger and the spraying element are situated inside the chamber. This device resolves the problem of the device of German Patent Specification No. 3213919 by having short starting and closing times.

SUMMARY OF THE INVENTION

The objective of the present invention is to provide methods and the cryogenic devices which are directed to carrying out the safe treatment on the whole body of one or several patients. The cryogenic chamber has preferable application in the medical cryogenic therapy, in particular in the therapy of pain and rheumatic disorders.

The present invention provides a cryogenic chamber with means for producing a low temperature by vaporizing liquefied gas or a mixture of gases inside or outside the cryogenic chamber to provide a cold breathable atmosphere in the chamber. Preferably, the low temperature inside the cryogenic chamber is generated by vaporizing cold liquefied nitrogen and a cold liquefied oxygen or a mixture of cold liquefied nitrogen and a cold liquefied oxygen, for example cold liquefied air, wherein the mixture of gases is a mixture suitable for breathing. A cold gas is produced by vaporizing cold liquefied gases or a cold liquefied mixture of gases, preferable of a composition similar to air. Changing the proportions within the mixture or changing the flow rate of the supplied liquefied gas allows producing atmosphere of cold air with the enhanced amount of oxygen. The composition of the atmosphere inside the cryogenic chamber can be adjusted using simple means, in particular using a control system to selectively open and close valves for introducing the gas into the chamber. It is possible to establish an atmosphere of a defined composition, while the composition is maintained unchanged during the therapeutic session. However, it is also possible to modify the composition of the atmosphere during the therapeutic session. The invention allows therapy with a mixture specific gasses having periods of higher amount of oxygen inside the cryogenic chamber. The cryogenic chamber preferably allows patients to walk inside the chamber.

Vaporization of cold liquefied gases or cold liquefied mixture of gases inside the cryogenic chamber generates a low temperature in a range of $-180°$ C. to $0°$ C., preferably $-60°$ C. to $-160°$ C., and the most preferably $-120°$ C. to $-160°$ C. The temperature inside the cryogenic chamber is preferably measured using a temperature sensor, and the measurement signal is provided to the control unit, which controls the amount of cold liquefied gases that need to be vaporized. Dispensing of the cold liquefied gases is performed by the controllable valve placed in the gas supplying line.

The device of the present invention comprises a cryogenic chamber and a system for introducing into the chamber a cooling agent, preferably a mixture of cold gases. The system preferably contains piping, nozzles, and/or heat exchangers for delivering the liquefied gases and/or vaporizing the gases or gas mixture into the chamber. The preferred device for carrying out the cryogenic therapy, particularly on the whole body of the patient, comprises a chamber having thermally insulated walls with an open upper part. The interior of the chamber contains a space having a low temperature cooling agent therein and a cryogenic cabin, which is separated from the space, and is cooled by the cooling agent.

In one embodiment, the device for carrying out the cryogenic therapy contains a chamber with an open upper part. The chamber has thermally insulated walls and containing a space with the a low temperature cooling agent. Also, inside the chamber there is a cryogenic treatment cabin, which is separated from the space and cooled in its whole volume by the cooling agent. The cooling agent is preferably in the form of the liquid carbon dioxide or liquid nitrogen evaporated, e.g. by the nozzles. Additionally, the chamber preferably contains, in the upper part, an air intake device which provides the breathing air for the patient or the patients.

In another embodiment, the chamber has, in its upper part, a movable cover which is preferably transparent, and chamber lighting elements. The cryogenic therapeutic cabin can also includes an emergency door situated in a side wall of the chamber which enables the access to disabled patients on wheelchairs. The chamber may also include monitoring and control systems for temperature and oxygen concentration to maintain the proper temperature and oxygen levels, and to protect the patient or patients from temperature extremes and oxygen deprivation. If the temperature or oxygen concentration reaches beyond the safe limits, an alarm can be activated and the chamber operation can be shut down automatically.

The methods according to the invention provide proper and effective treatment for the patient; and the devices of the invention provides proper supply to the therapeutic chamber wherein the loaded gas has optimal parameters for the treatment regimen. The process is economical by taking advantage of the deposition of low temperature gas phenomenon.

The method according to the present invention comprises introducing a patient into a cryogenic chamber and cooling the chamber with a mixture of cold gases, preferably a mixture of oxygen and nitrogen. The cold gas mixture preferably contains the similar amount of oxygen and nitrogen as air to allow safe breathing of a human inside the chamber. Preferably, the method comprises introducing the patient or patients along the transport route through the upper part of a chamber, and then through the interior of the chamber having thermally insulated walls. The chamber contains a space for depositing a low temperature cooling agent. The cooling agent has a very low temperature, preferably about −60° C. to −160° C. The exposure time for the patient depends of the treatment regimen, and preferably ranges from about 0.5 to 5 minutes. After treatment, the patient or the patients are led out of the treatment cabin through the interior of the chamber having the space with the deposited low temperature cooling agent, then along the transport route out of the chamber to a room temperature area.

It is advantageous to perform the cryogenic therapy, particularly on the whole body of the patient, according to the present invention because it allows for the correct treatment thanks to the preliminary cooling of the patient's body, which is conducted in the space in the chamber with the deposited low temperature cooling agent, after which the patient is introduced into the treatment cabin. After using the cabin, the patient is gradually led out to the normal temperature area through the space with the deposited low temperature cooling agent in the chamber.

It is advantageous to use the device for carrying out cryogenic therapy, particularly on the whole body of the patient, according to the present invention because it enables high efficiency by reducing the loss of heat while the patient enters and leaves the chamber through the upper part of the chamber, and limiting the space with the deposited low temperature cooling agent to the treatment chamber. The reduction of the loss of heat is obtained by using the movable transparent cover situated above the upper part of the chamber shielding it partially or completely while the patient or the patients are inside the cabin and when the cabin is empty. The lighting elements are situated in the internal surfaces of the chamber and allow for a comfortable environment for the patient. The emergency door situated in a side wall of the chamber also enables the direct exit of the patient from the cabin if needed.

BRIEF DESCRIPTION OF THE DRAWINGS

The subject matter of the invention is shown by way of example with the reference to the accompanying drawings wherein.

DETAILED DESCRIPTION OF THE PREFERRED EMBODIMENT

Figure 4:
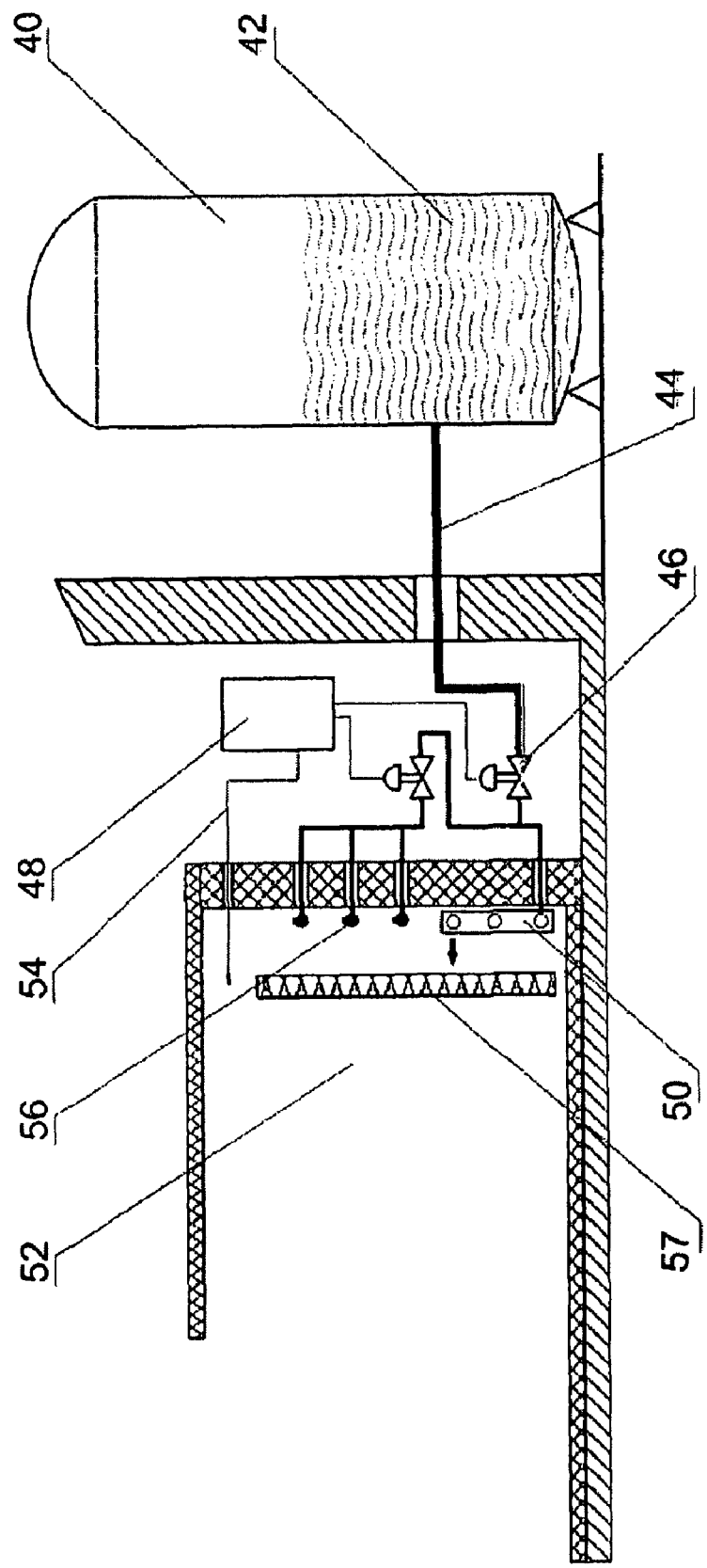
FIG. 4 shows one embodiment of the cryogenic chamber.

An embodiment of the present invention is shown in FIG. 4, where the device comprises a cryogenic chamber 52, preferably containing insulated walls. The chamber is cooled by a cooling agent 42 held in a tank 40. The mixture of gases preferably contains nitrogen and oxygen. Although FIG. 4 shows a single tank, each component of the cooling agent may be held separately and mixed in the chamber 52. In that case, there will be more than one tank, each holding a different component of the cooling agent. The cooling agent 42 is led into the chamber by a system of piping 44, valves, 46, heat exchanger 50, and nozzles 56. The nozzles 56 allow the gas to be vaporized by spraying to get the chamber more dynamic. Near the heat exchanger 50 there is a separating barrier 57 which separates the space in which treatment of a patient is carried out from the space in which the process of evaporation of liquefied gases occurs. This avoids directly contact of the patient with the gases in liquid form. Additionally, there is preferably a control system 48 for controlling the temperature and oxygen concentration in the chamber. This control system 48 communicates with a sensor 54 in the chamber 52 to control the valves 46 to the heat exchanger 50 and to the valves 56 to properly maintain the temperature and oxygen concentration in the chamber 52. Preferably, the cooling agent is a mixture of liquefied gases and has the same nitrogen and oxygen composition of air, i.e. approximately 21% oxygen and 79% nitrogen. In any event, the oxygen concentration should not be below 19% and should not exceed 24%. These gases can be premixed in the tank 40 or held in different tanks and mixed when vaporized into the chamber.

Figure 1:
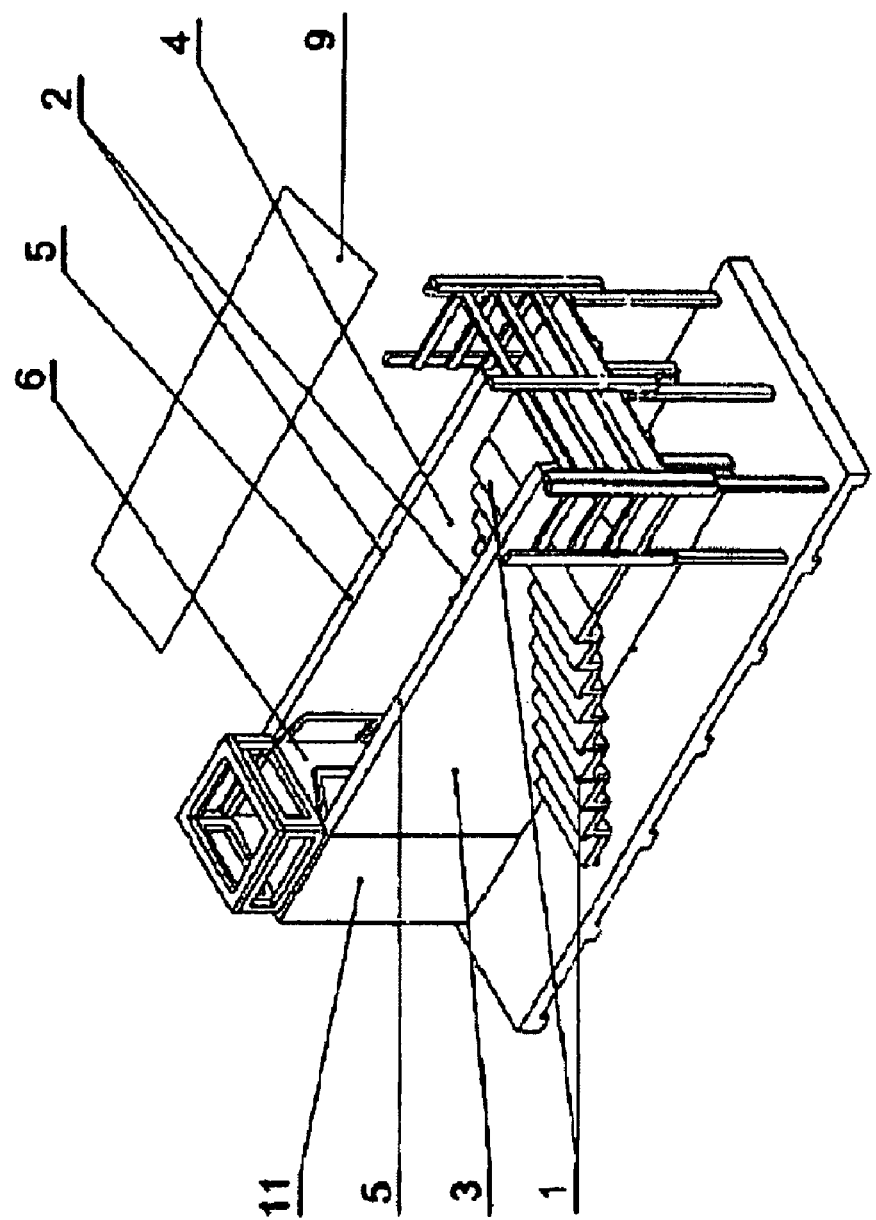
FIG. 1 shows a view of the treatment chamber.
Figure 2:
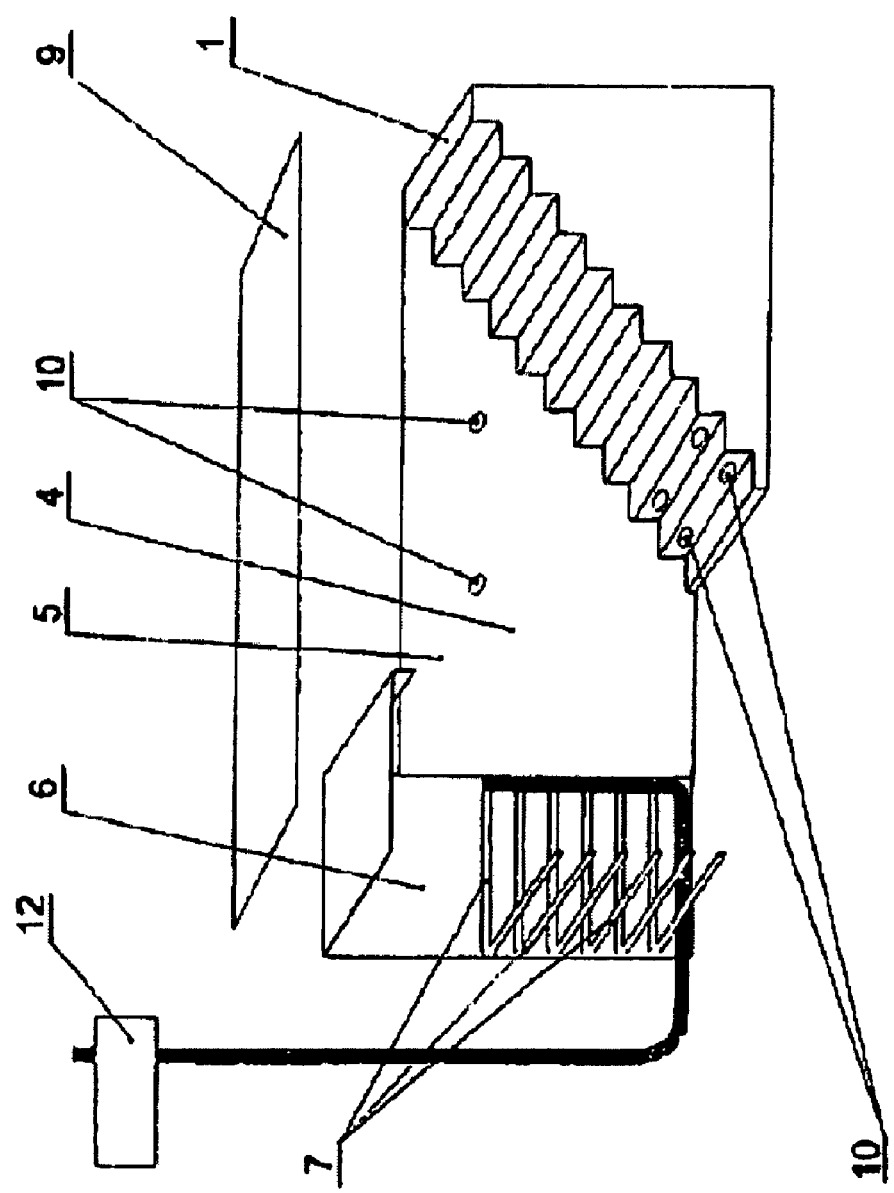
FIG. 2 shows a longitudinal section of the chamber.

In another embodiment, the device according to the invention is shown in the FIG. 1 and FIG. 2. This device contains a chamber 3, which is opened in the upper part 2. The chamber 3 has thermally insulated walls 5 and a space 4 with deposited low temperature cooling agent in the form of cold air. At one of the side walls 5, the chamber 3 has a transport route 1 which allows the patient to step down into the interior of the chamber 3 and to enter the space 4 with the deposited low temperature cooling agent. The patient is preliminarily transported to the low temperature space 4, and then introduced into a cryogenic therapeutic cabin 6 where the temperature is about −60° C. to −160° C. for a time period of about 0.5 to 5 minutes. The specific exposure time and temperature depends on the doctor's recommendations and the therapeutic regime being effected. Next, the patient leaves the cryogenic cabin 6 and after passing through the interior of the space 4 with the deposited low temperature cooling agent, the patient is gradually brought to room temperature by leaving the chamber through the transport route 1.

In one embodiment, the cryogenic therapeutic cabin 6 is situated inside the chamber 3 and is cooled by a cooling agent, preferably evaporating liquefied gases, from nozzles and pipe system 7. The cooling agent preferably has the same nitrogen and oxygen composition of air, i.e. approximately 21% oxygen and 79% nitrogen. In any event, the oxygen concentration should not be below 19% and should not exceed 24%. The cold gas mixture can be in liquid form, carried to the chamber by pipes and vaporized by nozzles and pipes into the chamber. Alternatively, the gas mixture can be vaporized into the heat exchanger prior to introduction into the chamber.

Figure 3:
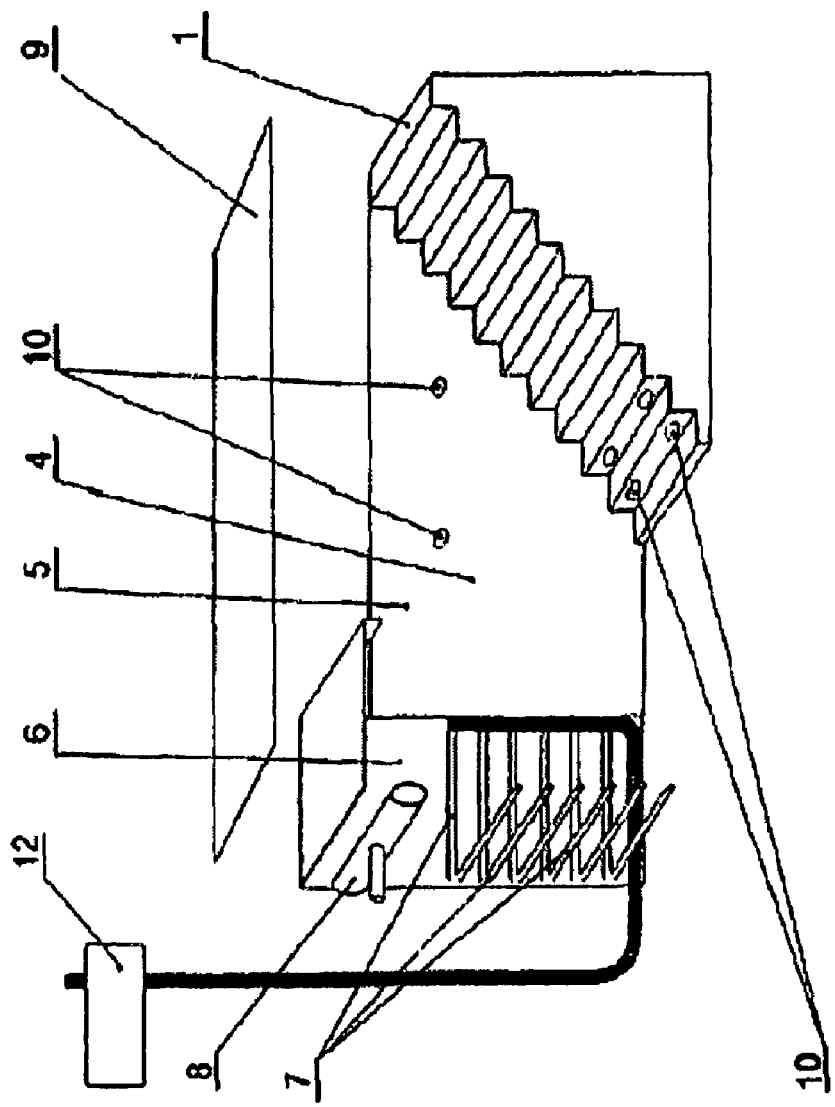
FIG. 3 shows a longitudinal section of the chamber with the air intake device.

In a preferred embodiment, a device according to the invention is shown in the FIG. 3, which has a cryogenic therapeutic cabin 6 situated inside the chamber 3. The cabin 6 is cooled in its whole volume by spraying a cooling agent, preferably in the form of liquid carbon dioxide cooled to about −60° C. or in the form of liquid nitrogen cooled to about −160° C. The spraying process is preferably carried out by nozzles 7. In the upper part of the cabin 6 is an intake device 8 which provides breathing air to the patient.

Preferably, the device according to the present invention has, in an upper part 2 of the chamber 3, a transparent movable cover 9 and lighting elements 10. The cryogenic therapeutic cabin 6 preferably has an emergency door 11 situated in a side surface of the chamber 3. It allows for the entry and exit of disabled patients using wheelchairs or other mobile device. The device also preferably has a monitoring and control system 12 for monitoring and controlling the temperature and the oxygen concentration for safeguarding the patient or the patients.

The device for the cryogenic therapy can be stationary or mobile adapted to building conditions.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What claimed is:

1. A cryogenic device comprising a chamber cooled by a mixture of liquefied gases, the gases creating atmosphere in which a patient is able to respire after their evaporation, wherein the chamber has a temperature of −60° C. to −160° C.

2. The device of claim 1, wherein the mixture of gases contains oxygen and nitrogen in proportion similar to air.

3. The device of claim 2, wherein the oxygen content in the chamber is not less than 19% and not more than 24%.

4. The device of claim 1, wherein the cooled mixture of gases is vaporized outside the chamber.

5. The device of claim 1, wherein the cooled mixture of gases is vaporized into the chamber from a liquid tank by nozzles.

6. The device of claim 1, further comprising a controller or controllers for controlling the temperature of the chamber and the gas concentration in the chamber.

7. A method for cooling a cryogenic chamber by introducing into the chamber a mixture of liquefied gases, the gases creating an atmosphere in which a patient is able to respire after their evaporation, wherein the chamber has a temperature of −60° C. to −160° C.

8. The method of claim 7, wherein the mixture of gases contains oxygen and nitrogen in proportion similar to air.

9. The method of claim 8, wherein the oxygen content in the chamber is not less than 19% and not more than 24%.

10. The method of claim 7, wherein the cooled mixture of gases is vaporized outside the chamber.

11. The method of claim 7, wherein the mixture of gases is vaporized into the chamber by nozzles.

12. The method of claim 7, further comprising a controller or controllers for controlling the temperature of the chamber and the gas concentration in the chamber.

\* \* \* \* \*